(12) United States Patent
Jepson (10) Patent No.: US 8,221,363 B2
(45) Date of Patent: Jul. 17, 2012

(54) LUER ACTIVATED DEVICE WITH VALVE ELEMENT UNDER TENSION

(75) Inventor: Steven C. Jepson, Palatine, IL (US)

(73) Assignee: Baxter Healthcare S.A., Glattpark (Opfikon) (CH)

( * ) Notice: Subject to any disclaimer, the term of this patent is extended or adjusted under 35 U.S.C. 154(b) by 1455 days.

(21) Appl. No.: 11/550,589

(22) Filed: Oct. 18, 2006

(65) Prior Publication Data
US 2008/0172005 A1   Jul. 17, 2008

(51) Int. Cl.
*A61M 5/00* (2006.01)
(52) U.S. Cl. .................................... 604/256; 604/249
(58) Field of Classification Search ........... 604/246–256
See application file for complete search history.

(56) References Cited

U.S. PATENT DOCUMENTS

| | | | |
|---|---|---|---|
| 4,176,588 A | 12/1979 | Baron | |
| 4,334,551 A | 6/1982 | Pfister | |
| 4,413,462 A | 11/1983 | Rose | |
| 4,475,548 A | 10/1984 | Muto | |
| 4,691,929 A | 9/1987 | Neumaier et al. | |
| 4,928,212 A | 5/1990 | Benavides | |
| 4,943,896 A | 7/1990 | Johnson | |
| 4,946,445 A | 8/1990 | Lynn | |
| 4,964,855 A | 10/1990 | Todd et al. | |
| 4,973,443 A | 11/1990 | Larson et al. | |
| 4,998,713 A | 3/1991 | Vaillancourt | |
| 4,998,927 A | 3/1991 | Vaillancourt | |
| 5,009,490 A | 4/1991 | Kouno et al. | |
| 5,019,325 A | 5/1991 | Larson et al. | |
| 5,046,456 A | 9/1991 | Heyman et al. | |
| D321,250 S | 10/1991 | Jepson et al. | |
| D321,251 S | 10/1991 | Jepson et al. | |
| 5,064,416 A | 11/1991 | Newgard et al. | |
| 5,065,783 A | 11/1991 | Ogle, II | |
| 5,100,394 A | 3/1992 | Dudar et al. | |
| 5,114,408 A | 5/1992 | Fleischhaker et al. | |
| 5,122,123 A | 6/1992 | Vaillancourt | |
| 5,135,489 A | 8/1992 | Jepson et al. | |
| 5,154,703 A | 10/1992 | Bonaldo | |
| 5,158,554 A | 10/1992 | Jepson et al. | |
| 5,171,234 A | 12/1992 | Jepson et al. | |
| 5,188,620 A | 2/1993 | Jepson et al. | |
| 5,199,947 A | 4/1993 | Lopez et al. | |
| 5,201,717 A | 4/1993 | Wyatt et al. | |

(Continued)

FOREIGN PATENT DOCUMENTS

CA          1105959          7/1981
(Continued)

*Primary Examiner* — Kevin C Sirmons
*Assistant Examiner* — Imani Hayman
(74) *Attorney, Agent, or Firm* — K&L Gates LLP (57) ABSTRACT

A luer activated device includes an inlet adapted to receive a male luer, an outlet associable with a fluid flow system, and a fluid flow path therebetween. The flow path is defined by an elastomeric flow controller extending between the inlet and outlet and maintained in a tensioned state. When a male luer is inserted into the inlet, some of the tension in the flow controller is relieved, allowing the flow path to deform and change in volume. The flow path is adapted such that the change in volume results in no net fluid displacement or minimal positive fluid displacement when the male luer is inserted into the inlet. Other aspects include tensioned flow controllers having a plurality of sealing layers for the inlet and methods of manufacturing valves having a tensioned fluid flow controller.

15 Claims, 8 Drawing Sheets

U.S. PATENT DOCUMENTS

| | | |
|---|---|---|
| 5,203,775 A | 4/1993 | Frank et al. |
| 5,211,638 A | 5/1993 | Dudar et al. |
| 5,242,393 A | 9/1993 | Brimhall et al. |
| 5,242,425 A | 9/1993 | White et al. |
| 5,242,432 A | 9/1993 | DeFrank |
| 5,251,873 A | 10/1993 | Atkinson et al. |
| 5,256,155 A | 10/1993 | Yerlikaya et al. |
| 5,269,763 A | 12/1993 | Boehmer et al. |
| 5,269,771 A | 12/1993 | Thomas et al. |
| 5,280,876 A | 1/1994 | Atkins |
| 5,290,254 A | 3/1994 | Vaillancourt |
| 5,295,657 A | 3/1994 | Atkinson |
| 5,295,658 A | 3/1994 | Atkinson et al. |
| 5,312,377 A | 5/1994 | Dalton |
| 5,323,264 A | 6/1994 | Kato |
| 5,324,270 A | 6/1994 | Kayan et al. |
| 5,344,414 A | 9/1994 | Lopez et al. |
| 5,360,413 A | 11/1994 | Leason et al. |
| 5,401,245 A | 3/1995 | Haining |
| 5,402,982 A | 4/1995 | Atkinson et al. |
| 5,411,499 A | 5/1995 | Dudar et al. |
| 5,417,673 A | 5/1995 | Gordon |
| 5,470,319 A | 11/1995 | Mayer |
| 5,487,731 A | 1/1996 | Denton |
| 5,514,109 A | 5/1996 | Mollenauer et al. |
| 5,533,708 A | 7/1996 | Atkinson et al. |
| 5,540,661 A | 7/1996 | Tomisaka et al. |
| 5,549,566 A | 8/1996 | Elias et al. |
| 5,549,651 A | 8/1996 | Lynn |
| 5,556,388 A | 9/1996 | Johlin, Jr. |
| 5,578,059 A | 11/1996 | Patzer |
| 5,602,016 A | 2/1997 | Isogai et al. |
| 5,609,584 A | 3/1997 | Gettig et al. |
| 5,616,129 A | 4/1997 | Mayer |
| 5,616,130 A | 4/1997 | Mayer |
| 5,676,346 A | 10/1997 | Leinsing |
| 5,677,141 A | 10/1997 | Isogai et al. |
| 5,685,866 A | 11/1997 | Lopez |
| 5,690,612 A | 11/1997 | Lopez et al. |
| 5,695,466 A | 12/1997 | Lopez et al. |
| 5,699,821 A | 12/1997 | Paradis |
| 5,700,248 A | 12/1997 | Lopez |
| 5,730,418 A | 3/1998 | Feith et al. |
| 5,738,663 A | 4/1998 | Lopez |
| 5,773,272 A | 6/1998 | Isogai et al. |
| RE35,841 E | 7/1998 | Frank et al. |
| 5,788,675 A | 8/1998 | Mayer |
| 5,797,897 A | 8/1998 | Jepson et al. |
| 5,820,601 A | 10/1998 | Mayer |
| 5,836,923 A | 11/1998 | Mayer |
| 5,865,807 A | 2/1999 | Blake, III |
| 5,873,862 A | 2/1999 | Lopez |
| 5,901,942 A | 5/1999 | Lopez |
| 5,928,204 A | 7/1999 | Lopez |
| 5,957,898 A | 9/1999 | Jepson et al. |
| 5,967,490 A | 10/1999 | Pike |
| 5,971,965 A | 10/1999 | Mayer |
| RE36,587 E | 2/2000 | Tanaka et al. |
| 6,019,748 A | 2/2000 | Lopez |
| 6,029,946 A | 2/2000 | Doyle |
| 6,036,171 A | 3/2000 | Weinheimer et al. |
| 6,039,302 A | 3/2000 | Cote, Sr. et al. |
| RE36,661 E | 4/2000 | Tanaka et al. |
| 6,048,335 A | 4/2000 | Mayer |
| 6,089,541 A | 7/2000 | Weinheimer et al. |
| 6,113,068 A | 9/2000 | Ryan |
| 6,132,403 A | 10/2000 | Lopez |
| 6,132,404 A | 10/2000 | Lopez |
| 6,146,396 A | 11/2000 | Konya et al. |
| 6,152,900 A | 11/2000 | Mayer |
| 6,162,251 A | 12/2000 | Kredovski |
| 6,171,287 B1 | 1/2001 | Lynn et al. |
| 6,177,037 B1 | 1/2001 | Mayer |
| 6,183,448 B1 | 2/2001 | Mayer |
| 6,187,476 B1 | 2/2001 | Pyun et al. |
| 6,210,624 B1 | 4/2001 | Mayer |
| 6,228,069 B1 | 5/2001 | Barth et al. |
| 6,245,048 B1 | 6/2001 | Fangrow, Jr. et al. |
| 6,261,268 B1 | 7/2001 | Mayer |
| 6,261,282 B1 | 7/2001 | Jepson et al. |
| 6,290,206 B1 | 9/2001 | Doyle |
| 6,299,132 B1 | 10/2001 | Weinheimer et al. |
| 6,325,782 B1 | 12/2001 | Lopez |
| 6,341,802 B1 | 1/2002 | Matkovich |
| 6,344,033 B1 | 2/2002 | Jepson et al. |
| 6,355,023 B1 | 3/2002 | Roth et al. |
| 6,364,869 B1 | 4/2002 | Bonaldo |
| 6,374,876 B2 | 4/2002 | Bynum |
| 6,383,168 B1 | 5/2002 | Landau et al. |
| 6,390,120 B1 | 5/2002 | Guala |
| 6,390,130 B1 | 5/2002 | Guala |
| 6,394,983 B1 | 5/2002 | Mayoral et al. |
| 6,394,992 B1 | 5/2002 | Sjoholm |
| 6,402,723 B1 | 6/2002 | Lampropoulos |
| 6,408,897 B1 | 6/2002 | Laurent et al. |
| 6,409,707 B1 | 6/2002 | Guala |
| 6,409,708 B1 | 6/2002 | Wessman |
| 6,423,053 B1 | 7/2002 | Lee |
| 6,428,520 B1 | 8/2002 | Lopez et al. |
| 6,440,107 B1 | 8/2002 | Trombley, III et al. |
| 6,467,732 B2 | 10/2002 | Tsukahara |
| 6,481,756 B1 | 11/2002 | Field et al. |
| 6,482,188 B1 | 11/2002 | Rogers et al. |
| 6,485,472 B1 | 11/2002 | Richmond |
| 6,486,630 B2 | 11/2002 | Takagi |
| 6,491,668 B1 | 12/2002 | Paradis |
| 6,508,807 B1 | 1/2003 | Peters |
| 6,520,932 B2 | 2/2003 | Taylor |
| 6,536,805 B2 | 3/2003 | Matkovich |
| 6,537,258 B1 | 3/2003 | Guala |
| 6,539,248 B1 | 3/2003 | Moroski |
| 6,541,802 B2 | 4/2003 | Doyle |
| 6,543,745 B1 | 4/2003 | Enerson |
| 6,544,236 B1 | 4/2003 | Cragg et al. |
| 6,569,118 B2 | 5/2003 | Johnson et al. |
| 6,569,125 B2 | 5/2003 | Jepson et al. |
| RE38,145 E | 6/2003 | Lynn |
| 6,572,590 B1 | 6/2003 | Stevens et al. |
| 6,572,591 B2 | 6/2003 | Mayer |
| 6,572,592 B1 | 6/2003 | Lopez |
| 6,581,906 B2 | 6/2003 | Pott et al. |
| 6,585,229 B2 | 7/2003 | Cote, Sr. et al. |
| 6,595,954 B1 | 7/2003 | Luther et al. |
| 6,595,964 B2 | 7/2003 | Finley et al. |
| 6,599,273 B1 | 7/2003 | Lopez |
| 6,605,076 B1 | 8/2003 | Jepson et al. |
| 6,609,696 B2 | 8/2003 | Enerson |
| 6,620,119 B1 | 9/2003 | Utterberg et al. |
| 6,626,418 B2 | 9/2003 | Kiehne |
| 6,634,033 B2 | 10/2003 | Mizuno et al. |
| 6,635,044 B2 | 10/2003 | Lopez |
| 6,638,244 B1 | 10/2003 | Reynolds |
| 6,638,258 B2 | 10/2003 | Schwartz et al. |
| 6,651,956 B2 | 11/2003 | Miller |
| 6,655,655 B1 | 12/2003 | Matkovich et al. |
| 6,666,839 B2 | 12/2003 | Utterberg et al. |
| 6,669,673 B2 | 12/2003 | Lopez |
| 6,669,681 B2 * | 12/2003 | Jepson et al. ................. 604/533 |
| 6,673,059 B2 | 1/2004 | Guala |
| 6,679,529 B2 | 1/2004 | Johnson et al. |
| 6,681,810 B2 | 1/2004 | Weston |
| 6,682,509 B2 | 1/2004 | Lopez |
| 6,695,817 B1 | 2/2004 | Fangrow, Jr. |
| 6,699,222 B1 | 3/2004 | Jones et al. |
| 6,706,022 B1 | 3/2004 | Leinsing et al. |
| 6,716,187 B1 | 4/2004 | Jorgensen et al. |
| 6,716,189 B1 | 4/2004 | Jarvik et al. |
| 6,722,705 B2 | 4/2004 | Korkor |
| 6,723,074 B1 | 4/2004 | Halseth |
| 6,726,651 B1 | 4/2004 | Robinson et al. |
| 6,726,672 B1 | 4/2004 | Hanly et al. |
| 6,730,883 B2 | 5/2004 | Brown et al. |
| 6,745,998 B2 | 6/2004 | Doyle |
| 6,746,438 B1 | 6/2004 | Arnissolle |
| 6,755,391 B2 | 6/2004 | Newton et al. |
| 6,758,833 B2 | 7/2004 | Lopez |
| 6,770,051 B2 | 8/2004 | Hughes et al. |

| | | |
|---|---|---|
| 6,802,490 B2 | 10/2004 | Leinsing et al. |
| 6,802,836 B2 | 10/2004 | Bouphavichith et al. |
| 6,808,161 B1 | 10/2004 | Hishikawa |
| 6,808,509 B1 | 10/2004 | Davey |
| 6,811,139 B2 | 11/2004 | Hishikawa |
| 6,814,726 B1 | 11/2004 | Lauer |
| 6,827,709 B2 | 12/2004 | Fujii |
| 6,827,710 B1 | 12/2004 | Mooney et al. |
| 6,834,842 B2 | 12/2004 | Houde |
| 6,840,501 B2 | 1/2005 | Doyle |
| 6,843,513 B2 | 1/2005 | Guala |
| 6,866,656 B2 | 3/2005 | Tingey et al. |
| 6,869,426 B2 | 3/2005 | Ganem |
| 6,871,087 B1 | 3/2005 | Hughes et al. |
| 6,874,522 B2 | 4/2005 | Anderson et al. |
| 6,878,905 B2 | 4/2005 | Brown et al. |
| 6,880,801 B2 | 4/2005 | Matkovich et al. |
| 6,883,778 B1 | 4/2005 | Newton et al. |
| 6,893,056 B2 | 5/2005 | Guala |
| 6,902,207 B2 | 6/2005 | Lickliter |
| 6,908,459 B2 | 6/2005 | Harding et al. |
| 6,911,025 B2 | 6/2005 | Miyahara |
| 6,916,309 B2 | 7/2005 | Fangrow, Jr. |
| 6,918,500 B2 | 7/2005 | Okiyama |
| 6,932,795 B2 | 8/2005 | Lopez et al. |
| 6,953,450 B2 | 10/2005 | Baldwin et al. |
| 6,955,669 B2 | 10/2005 | Curutcharry |
| 6,960,198 B2 | 11/2005 | Sarmiento |
| 6,964,406 B2 | 11/2005 | Doyle |
| 6,969,381 B2 | 11/2005 | Voorhees |
| 6,972,001 B2 | 12/2005 | Emig et al. |
| 6,974,446 B2 | 12/2005 | Hommann et al. |
| 6,994,315 B2 | 2/2006 | Ryan et al. |
| 7,004,934 B2 | 2/2006 | Vaillancourt |
| 7,008,406 B2 | 3/2006 | Mayer |
| 7,014,169 B2 | 3/2006 | Newton et al. |
| 7,025,744 B2 | 4/2006 | Utterberg et al. |
| 7,033,339 B1 | 4/2006 | Lynn |
| 7,037,302 B2 | 5/2006 | Vaillancourt et al. |
| 7,041,087 B2 | 5/2006 | Henderson et al. |
| 7,044,441 B2 | 5/2006 | Doyle |
| 7,044,937 B1 | 5/2006 | Kirwan et al. |
| 7,081,600 B2 | 7/2006 | Brown et al. |
| 7,083,605 B2 | 8/2006 | Miyahara |
| 7,090,191 B2 | 8/2006 | Matkovich et al. |
| 7,097,209 B2 | 8/2006 | Sparrman et al. |
| 7,100,891 B2 | 9/2006 | Doyle |
| 7,104,520 B2 | 9/2006 | Leinsing et al. |
| RE39,334 E | 10/2006 | Lynn |
| 7,114,701 B2 | 10/2006 | Peppel |
| 7,118,560 B2 | 10/2006 | Bonaldo |
| 7,128,348 B2 | 10/2006 | Kawamura et al. |
| 7,137,974 B2 | 11/2006 | Almasian et al. |
| 7,140,592 B2 | 12/2006 | Mitchell |
| 7,153,296 B2 | 12/2006 | Mitchell |
| 7,156,826 B2 | 1/2007 | Ishii et al. |
| 7,160,272 B1 | 1/2007 | Eyal et al. |
| RE39,499 E | 2/2007 | Racz |
| 7,172,572 B2 | 2/2007 | Diamond et al. |
| 7,174,923 B2 | 2/2007 | Schorn et al. |
| 7,175,615 B2 | 2/2007 | Hanly et al. |
| 7,182,313 B2 | 2/2007 | Doyle |
| 7,184,825 B2 | 2/2007 | Leinsing et al. |
| 7,396,348 B2 * | 7/2008 | Newton et al. ............... 604/256 |
| 2001/0045539 A1 | 11/2001 | Doyle |
| 2001/0049508 A1 | 12/2001 | Fangrow et al. |
| 2001/0051791 A1 | 12/2001 | Azzolini |
| 2001/0051793 A1 | 12/2001 | Weston |
| 2002/0007157 A1 | 1/2002 | Azzolini |
| 2002/0024036 A1 | 2/2002 | Rohrbough et al. |
| 2002/0032433 A1 | 3/2002 | Lopez |
| 2002/0038114 A1 | 3/2002 | Segura |
| 2002/0062106 A1 | 5/2002 | Chu et al. |
| 2002/0082586 A1 | 6/2002 | Finley et al. |
| 2002/0099360 A1 | 7/2002 | Bierman |
| 2002/0108614 A1 | 8/2002 | Schultz |
| 2002/0115981 A1 | 8/2002 | Wessman |
| 2002/0115984 A1 | 8/2002 | Guala |
| 2002/0117645 A1 | 8/2002 | Kiehne |
| 2002/0128595 A1 | 9/2002 | Weston et al. |
| 2002/0128607 A1 | 9/2002 | Haury et al. |
| 2002/0133124 A1 | 9/2002 | Leinsing et al. |
| 2002/0138047 A1 | 9/2002 | Lopez |
| 2002/0143300 A1 | 10/2002 | Trombley et al. |
| 2002/0143301 A1 | 10/2002 | Lopez |
| 2002/0147429 A1 | 10/2002 | Cowan et al. |
| 2002/0147431 A1 | 10/2002 | Lopez et al. |
| 2002/0153503 A1 | 10/2002 | Newton et al. |
| 2002/0156431 A1 | 10/2002 | Feith et al. |
| 2002/0161334 A1 | 10/2002 | Castellano et al. |
| 2002/0193752 A1 | 12/2002 | Lynn |
| 2003/0028156 A1 | 2/2003 | Juliar |
| 2003/0032940 A1 | 2/2003 | Doyle |
| 2003/0036735 A1 | 2/2003 | Jepson et al. |
| 2003/0050610 A1 | 3/2003 | Newton et al. |
| 2003/0060779 A1 | 3/2003 | Richmond |
| 2003/0060804 A1 | 3/2003 | Vaillancourt |
| 2003/0066978 A1 | 4/2003 | Enerson |
| 2003/0066980 A1 | 4/2003 | Hishikawa |
| 2003/0085372 A1 | 5/2003 | Newton |
| 2003/0093061 A1 | 5/2003 | Ganem |
| 2003/0098430 A1 | 5/2003 | Leinsing et al. |
| 2003/0105452 A1 | 6/2003 | Mayer |
| 2003/0109853 A1 | 6/2003 | Harding et al. |
| 2003/0120221 A1 | 6/2003 | Vaillancourt |
| 2003/0127620 A1 | 7/2003 | Houde |
| 2003/0141477 A1 | 7/2003 | Miller |
| 2003/0144626 A1 | 7/2003 | Hanson et al. |
| 2003/0144647 A1 | 7/2003 | Miyahara |
| 2003/0181850 A1 | 9/2003 | Diamond et al. |
| 2003/0181854 A1 | 9/2003 | Sauvageau |
| 2003/0183795 A1 | 10/2003 | Doyle |
| 2003/0195478 A1 | 10/2003 | Russo |
| 2003/0199835 A1 | 10/2003 | Leinsing et al. |
| 2003/0208165 A1 | 11/2003 | Christensen et al. |
| 2003/0209681 A1 | 11/2003 | Leinsing et al. |
| 2003/0216712 A1 | 11/2003 | Kessler et al. |
| 2003/0225379 A1 | 12/2003 | Schaffer et al. |
| 2003/0236497 A1 | 12/2003 | Fremming et al. |
| 2004/0006330 A1 | 1/2004 | Fangrow |
| 2004/0019344 A1 | 1/2004 | Peterson et al. |
| 2004/0030321 A1 | 2/2004 | Fangrow |
| 2004/0068238 A1 | 4/2004 | Utterberg |
| 2004/0068239 A1 | 4/2004 | Utterberg |
| 2004/0073174 A1 | 4/2004 | Lopez |
| 2004/0073176 A1 | 4/2004 | Utterberg |
| 2004/0092886 A1 | 5/2004 | Mayer |
| 2004/0102738 A1 | 5/2004 | Dikeman et al. |
| 2004/0111078 A1 | 6/2004 | Miyahara |
| 2004/0116869 A1 | 6/2004 | Heinz et al. |
| 2004/0122418 A1 | 6/2004 | Voorhees |
| 2004/0124388 A1 | 7/2004 | Kiehne |
| 2004/0124389 A1 | 7/2004 | Phillips |
| 2004/0138641 A1 | 7/2004 | Patzer |
| 2004/0162517 A1 | 8/2004 | Furst et al. |
| 2004/0162540 A1 | 8/2004 | Walenciak et al. |
| 2004/0171993 A1 | 9/2004 | Bonaldo |
| 2004/0172006 A1 | 9/2004 | Bonaldo |
| 2004/0186458 A1 | 9/2004 | Hiejima et al. |
| 2004/0193119 A1 | 9/2004 | Canaud et al. |
| 2004/0199126 A1 | 10/2004 | Harding et al. |
| 2004/0204699 A1 | 10/2004 | Hanly et al. |
| 2004/0206924 A1 | 10/2004 | Newton et al. |
| 2004/0210194 A1 | 10/2004 | Bonnette et al. |
| 2004/0225274 A1 | 11/2004 | Jansen et al. |
| 2004/0227120 A1 | 11/2004 | Raybuck |
| 2004/0236314 A1 | 11/2004 | Saab |
| 2004/0243065 A1 | 12/2004 | McConnell et al. |
| 2004/0243069 A1 | 12/2004 | Feith et al. |
| 2004/0243070 A1 | 12/2004 | Lopez |
| 2004/0249349 A1 | 12/2004 | Wentling |
| 2004/0254534 A1 | 12/2004 | Bjorkman et al. |
| 2004/0260243 A1 | 12/2004 | Rickerd |
| 2004/0260266 A1 | 12/2004 | Cuschieri et al. |
| 2005/0010168 A1 | 1/2005 | Kendall |
| 2005/0015070 A1 | 1/2005 | Delnevo et al. |
| 2005/0021000 A1 | 1/2005 | Adair et al. |
| 2005/0033267 A1 | 2/2005 | Decaria |

| | | |
|---|---|---|
| 2005/0033268 A1 | 2/2005 | Decaria |
| 2005/0033269 A1 | 2/2005 | Decaria |
| 2005/0038397 A1 | 2/2005 | Newton et al. |
| 2005/0059952 A1 | 3/2005 | Giuliano et al. |
| 2005/0087715 A1 | 4/2005 | Doyle |
| 2005/0090805 A1 | 4/2005 | Shaw et al. |
| 2005/0096585 A1 | 5/2005 | Schon et al. |
| 2005/0107770 A1 | 5/2005 | Schweikert et al. |
| 2005/0119613 A1 | 6/2005 | Moenning et al. |
| 2005/0121638 A1 | 6/2005 | Doyle |
| 2005/0124935 A1 | 6/2005 | McMichael |
| 2005/0124942 A1 | 6/2005 | Richmond |
| 2005/0124943 A1 | 6/2005 | Yang |
| 2005/0151105 A1* | 7/2005 | Ryan et al. ............ 251/149.6 |
| 2005/0154372 A1 | 7/2005 | Minezaki |
| 2005/0159710 A1 | 7/2005 | Utterberg |
| 2005/0165365 A1 | 7/2005 | Newton et al. |
| 2005/0171487 A1 | 8/2005 | Haury et al. |
| 2005/0209555 A1 | 9/2005 | Middleton et al. |
| 2005/0228362 A1 | 10/2005 | Vaillancourt |
| 2005/0256460 A1 | 11/2005 | Rome et al. |
| 2005/0256461 A1 | 11/2005 | DiFiore et al. |
| 2005/0261637 A1 | 11/2005 | Miller |
| 2005/0261665 A1 | 11/2005 | Voorhees |
| 2005/0267445 A1 | 12/2005 | Mendels |
| 2006/0015086 A1 | 1/2006 | Rasmussen et al. |
| 2006/0025724 A1 | 2/2006 | Chen |
| 2006/0025751 A1 | 2/2006 | Roy et al. |
| 2006/0027270 A1 | 2/2006 | Truitt et al. |
| 2006/0047251 A1 | 3/2006 | Bickford-Smith et al. |
| 2006/0074386 A1 | 4/2006 | Wollmann |
| 2006/0089603 A1 | 4/2006 | Truitt et al. |
| 2006/0089604 A1 | 4/2006 | Guerrero |
| 2006/0089605 A1 | 4/2006 | Fitzgerald |
| 2006/0111694 A1 | 5/2006 | Fukai et al. |
| 2006/0129109 A1 | 6/2006 | Shaw et al. |
| 2006/0129112 A1 | 6/2006 | Lynn |
| 2006/0142735 A1 | 6/2006 | Whitley |
| 2006/0149213 A1 | 7/2006 | Raybuck |
| 2006/0161115 A1 | 7/2006 | Fangrow |
| 2006/0173420 A1 | 8/2006 | Fangrow |
| 2006/0178645 A1 | 8/2006 | Peppel |
| 2006/0184139 A1 | 8/2006 | Quigley et al. |
| 2006/0184140 A1 | 8/2006 | Okiyama |
| 2006/0200072 A1 | 9/2006 | Peppel |
| 2006/0200095 A1 | 9/2006 | Steube |
| 2006/0200096 A1 | 9/2006 | Fangrow |
| 2006/0206058 A1 | 9/2006 | Lopez |
| 2006/0206059 A1 | 9/2006 | Lopez |
| 2006/0211997 A1 | 9/2006 | Fangrow |
| 2006/0211998 A1 | 9/2006 | Fangrow |
| 2006/0211999 A1 | 9/2006 | Fangrow |
| 2006/0212000 A1 | 9/2006 | Fangrow |
| 2006/0212001 A1 | 9/2006 | Fangrow |
| 2006/0212002 A1 | 9/2006 | Fangrow |
| 2006/0212003 A1 | 9/2006 | Fangrow |
| 2006/0212005 A1 | 9/2006 | Fangrow |
| 2006/0212006 A1 | 9/2006 | Fangrow et al. |
| 2006/0217671 A1 | 9/2006 | Peppel |
| 2006/0217679 A1 | 9/2006 | Hanly et al. |
| 2006/0217683 A1 | 9/2006 | Patania |
| 2006/0229571 A1 | 10/2006 | Peppel |
| 2006/0229590 A1 | 10/2006 | Roy |
| 2006/0264842 A1 | 11/2006 | Fangrow |
| 2006/0264843 A1 | 11/2006 | Fangrow |
| 2006/0264844 A1 | 11/2006 | Fangrow |
| 2006/0264845 A1 | 11/2006 | Lopez |
| 2006/0264846 A1 | 11/2006 | Lopez |
| 2006/0264847 A1 | 11/2006 | Lopez |
| 2006/0264848 A1 | 11/2006 | Fangrow |
| 2006/0264890 A1 | 11/2006 | Moberg et al. |
| 2006/0264891 A1 | 11/2006 | Lopez |
| 2006/0264892 A1 | 11/2006 | Lopez |
| 2006/0264894 A1 | 11/2006 | Moberg et al. |
| 2006/0264908 A1 | 11/2006 | Ishii et al. |
| 2006/0264909 A1 | 11/2006 | Fangrow |
| 2006/0264910 A1 | 11/2006 | Fangrow |
| 2006/0270999 A1 | 11/2006 | Fangrow |
| 2006/0271012 A1 | 11/2006 | Canaud |
| 2006/0271015 A1 | 11/2006 | Mantell |
| 2006/0271016 A1 | 11/2006 | Fangrow |
| 2006/0276757 A1 | 12/2006 | Fangrow |
| 2006/0276758 A1 | 12/2006 | Fangrow |
| 2006/0287638 A1 | 12/2006 | Aneas |
| 2006/0287639 A1 | 12/2006 | Sharp |
| 2006/0293629 A1 | 12/2006 | Cote et al. |
| 2006/0293640 A1 | 12/2006 | Greco |
| 2007/0032775 A1 | 2/2007 | Niedospial et al. |
| 2007/0032776 A1 | 2/2007 | Skinner et al. |
| 2007/0038189 A1 | 2/2007 | Bartholomew |
| 2007/0043334 A1 | 2/2007 | Guala |
| 2007/0060898 A1 | 3/2007 | Shaughnessy et al. |
| 2007/0060902 A1 | 3/2007 | Brandenburger et al. |
| 2007/0060904 A1 | 3/2007 | Vedrine et al. |
| 2007/0073242 A1 | 3/2007 | Andersen et al. |
| 2007/0078393 A1 | 4/2007 | Lynch et al. |
| 2007/0078429 A1 | 4/2007 | Sharp |
| 2007/0083157 A1 | 4/2007 | Belley et al. |
| 2007/0088252 A1 | 4/2007 | Pestotnik et al. |
| 2007/0088292 A1 | 4/2007 | Fangrow |
| 2007/0088293 A1 | 4/2007 | Fangrow |
| 2007/0088294 A1 | 4/2007 | Fangrow |
| 2007/0088313 A1 | 4/2007 | Zinger et al. |
| 2007/0088324 A1 | 4/2007 | Fangrow |
| 2007/0088325 A1 | 4/2007 | Fangrow |
| 2007/0088327 A1 | 4/2007 | Guala |
| 2007/0093764 A1 | 4/2007 | Guerrero |
| 2007/0100294 A1 | 5/2007 | Sugita et al. |
| 2007/0112311 A1 | 5/2007 | Harding et al. |
| 2007/0112312 A1 | 5/2007 | Fangrow |
| 2007/0112313 A1 | 5/2007 | Fangrow |
| 2007/0112314 A1 | 5/2007 | Harding et al. |
| 2007/0112332 A1 | 5/2007 | Harding et al. |
| 2007/0112333 A1 | 5/2007 | Hoang et al. |
| 2007/0129705 A1 | 6/2007 | Trombley et al. |
| 2007/0156112 A1 | 7/2007 | Walsh |
| 2007/0156118 A1 | 7/2007 | Ramsey et al. |

FOREIGN PATENT DOCUMENTS

| | | |
|---|---|---|
| DE | 855319 | 11/1952 |
| DE | 8425197 | 10/1985 |
| DE | 3740269 | 6/1989 |
| EP | 0114677 | 8/1984 |
| EP | 0237321 | 9/1987 |
| EP | 0309771 | 4/1989 |
| EP | 0367549 | 10/1989 |
| EP | 0399119 | 11/1990 |
| EP | 0438909 | 12/1990 |
| EP | 0446463 | 12/1990 |
| EP | 1733749 A1 | 12/2006 |
| GB | 2034185 | 6/1980 |
| WO | 86/01712 | 3/1986 |
| WO | 86/03416 | 6/1986 |
| WO | 93/11828 | 6/1993 |
| WO | 97/21463 | 6/1997 |
| WO | 97/21464 | 6/1997 |
| WO | 98/26835 | 6/1998 |
| WO | 99/58186 | 11/1999 |
| WO | 02/04065 | 1/2002 |
| WO | 03/086528 | 10/2003 |

* cited by examiner

LUER ACTIVATED DEVICE WITH VALVE ELEMENT UNDER TENSION

FIELD OF THE INVENTION

The present invention relates generally to luer activated devices or valves that allow for the bi-directional transfer of fluids to and from medical fluid flow systems.

BACKGROUND OF THE INVENTION

Luer activated devices (LAD) or valves (LAV) are commonly used in association with medical fluid containers and medical fluid flow systems that are connected to patients or other subjects undergoing diagnostic, therapeutic or other medical procedures. A LAD can be attached to or part of a fluid container or a medical fluid flow system to simplify the addition of fluids to or withdrawal of fluids from the fluid flow system.

Within the medical field there are a wide variety of medical fluid flow systems, serving a variety of functions. One of the more common uses of LADs are in association with fluid flow systems that are used for the intravenous administration of fluids, such as saline, antibiotics, or any number of other medically-related fluids, to a patient. These flow systems are commonly referred to as intravenous or "IV" fluid administration sets, and use plastic tubing to connect a phlebotomized subject to one or more medical fluid sources, such as intravenous solution or medicament containers.

Typically, such intravenous administration sets include one or more LADs providing needless access to the fluid flow path to allow fluid to be added to or withdrawn from the IV tubing. The absence of a needle for injecting or withdrawing fluid has the important advantage of reducing the incidence of needle stick injuries to medical personnel. A LAD typically includes a tapered female luer component, such as the inlet into a valve housing, that accepts and mates with a tapered male luer of a medical infusion or aspiration device, such as a needleless syringe or a administration set tubing brand.

There are certain characteristics and qualities of LADs that are highly desirable. For example, the LAD should provide a sufficient microbial barrier for the full service life of the valve. It is desirable that the microbial barrier be conducive to the application of standard aseptic techniques preformed by clinicians during the use of the device. For example, the geometry of the LAD should be such that it is easily swabbable and reduces the potential of entrapping particulates or contaminants that cannot be cleanly swabbed clear prior to use. In addition, the LAD should not permit cross contamination between the male luer and the surfaces of the aseptic fluid path.

Furthermore, it is highly desirable that the LAD be substantially devoid of any interstitial space or any other "dead space" that cannot be flushed, or that such interstitial space be physically isolated from the fluid flow path. Such interstitial space has the potential of providing an environment for undesired microbial growth. In addition, the LAD should have a geometry that allows it to be sufficiently flushed so as to clear the dynamic fluid path and adjacent areas of residual blood or intravenous fluids to prevent undesired microbial growth.

LAD's are commonly used with intravenous catheters that provide access to a patient's vascular system. In such systems, another desirable feature of a LAD is minimal displacement of fluid during insertion and removal of the male luer. In certain situations, it is preferable that the LAD be a neutral/neutral device in that there is zero or only a very slight displacement of fluid during both insertion and removal of the male luer. In other situations it can be desirable for the LAD to produce a positive displacement of fluid from the valve housing during the insertion and removal of the male luer. The LAD also preferably prevents blood reflux into the catheter. Reflux is known to reduce the efficiency of the catheter, contribute to catheter clotting and also contribute to catheter related bloodstream infections.

In most situations it is preferred that the LAD be ergonomically dimensioned to be completely activated by a wide range of ISO compliant male luer lock adaptors. However, there may some instances when the LAD is specifically designed to be activated by a male luer lock that is not ISO complaint. Another desirable characteristic of a LAD is the ability of the LAD to seal against pressure contained within a fluid system to which the LAD is connected. For example, it is desirable to be leak resistance to positive pressures ranging from 10 to 45 psi and to negative pressures or vacuum from 1 to 5 psi. The LAD also preferably has a geometry that allows for easy priming and flushing that does not require any additional manipulations to remove residual air bubbles from the tubing system.

These and other desirable characteristics, which may be used separately or in combination, is preferably present over the full service life of the valve. When used in connection with an IV set or catheter, the LAD may go through many connections and disconnections. It is desirable that the life of an LAD last through upwards to about 100 connections and disconnections or 96 hours of dwell time.

As described more fully below, the fluid access devices of the present invention provides important advances in the safe and efficient administration or withdrawal of medical fluids to or from a fluid flow system.

SUMMARY OF THE INVENTION

In accordance with one aspect of the present invention, a medical valve for the bi-directional transfer of fluid is provided with a valve housing having an inlet adapted for receiving a male luer, an outlet and a passageway therethrough. A fluid flow controller is received within the valve housing and has a valve element fixedly attached to the inlet. The valve element has a resealable aperture for receiving a male luer and sealing the inlet. An extending portion extends away from the valve element and is fixedly attached to the outlet to define a fluid flow path in communication with the aperture and the outlet. The fluid flow controller is maintained in a tensioned state within the valve housing, such that insertion of a male luer into the inlet decreases the tension in at least a portion of the fluid flow controller.

According to another aspect of the present invention, a medical valve for the bi-directional transfer of fluid is provided with a valve housing having an inlet adapted for receiving a male luer. A fluid flow controller associated with the valve housing has a valve element fixedly attached to the inlet in a tensioned state. The valve element has a first sealing layer defining a first resealable aperture, a second sealing layer defining a second resealable aperture, and a channel therebetween and in communication with both apertures. The channel is substantially closed in the tensioned state and open in an untensioned state.

According to yet another aspect of the present invention, a method of manufacturing a medical valve involves providing a fluid flow controller having a valve element and an extending portion defining a fluid flow path. The valve element is fixedly attached to an upper portion of a valve housing so as to seal an inlet of the upper housing portion. The fluid flow controller is stretched away from the inlet and a lower housing portion is placed over the extending portion of the fluid flow controller so that the extending portion extends into an outlet of the lower housing portion. The lower housing portion is fixedly attached to the lower housing portion and a section of the extending portion is fixedly attached to the outlet, thereby maintaining the fluid flow controller in a tensioned state.

BRIEF DESCRIPTION OF THE DRAWINGS

Turning now to a more detailed description of the various embodiments of the present invention illustrated in the attached drawings, of which.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for teaching one skilled in the art to variously employ the present invention in virtually any appropriate manner.

Figure 1:
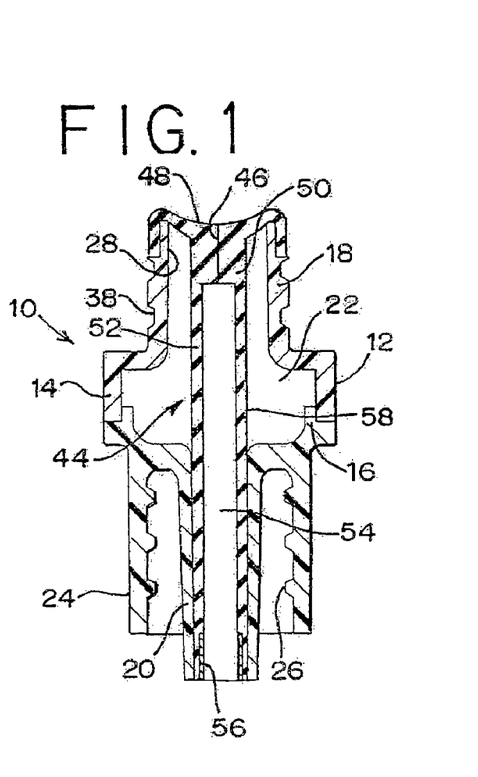
FIG. 1 is a cross-sectional view of one embodiment of a luer activated device of the present invention.

FIG. 1 generally illustrates a first embodiment of a luer activated device (LAD) or valve of the present invention, generally designated as 10. The LAD 10 includes a generally tubular valve housing 12 preferably comprised of a rigid material, such as plastic or other suitable material. The LAD 10 is provided as a combination of a joined upper housing portion 14 and a lower housing portion 16. The LAD 10 also includes an inlet 18, an outlet 20, and a passageway 22 defined therebetween. The terms "inlet" and "outlet" are not to be interpreted as limiting the LAD 10 to applications involving fluid flow in a particular direction, e.g., from the inlet 18 to the outlet 20, because LAD's according to the present invention may be used in applications involving fluid flow from the inlet 18 to the outlet 20 or from the outlet 20 to the inlet 18.

The outlet 20 is adapted to be connected to any of a number of fluid flow systems, so the exact configuration of the outlet 20 will vary according to the nature of the fluid flow system to which it is to be connected. For example, the illustrated outlet 20 is suitable for use in connecting the valve 10 to an IV administrative tubing set (not illustrated). In the embodiment of FIG. 1, the outlet 20 includes a skirt 24 defining an internal thread 26, which may be adapted to engage an external thread of the associated fluid flow system (not illustrated). Of course, the outlet 20 may be provided with a different configuration, a different locking system, or without a locking system, depending on the anticipated usage of the valve 10.

The inlet 18 includes an opening 28 adapted to receive a male luer 30 (FIGS. 2 and 3) according to known structure and operation. The inlet 18 and male luer 30 preferably conform functionally to ISO and/or ANSI standards. In general the inlet 18 is unable to conform dimensionally to ISO luer standards as there would be insufficient volume to house the septum displacement upon insertion of a luer tip.

The male luer 30 has a hollow channel 32 defined by a generally tubular wall 34. The wall 34 preferably has a substantially smooth outer surface 36 which is typically cylindrical or conical. The inlet 18 may include external threads 38, in which case a portion of the luer wall 34 may be surrounded by a collar member 40 (FIGS. 2 and 3) having internal threads 42 adapted to removably lock the male luer 30 to the inlet 18. Other locking mechanisms may also be incorporated into LAD's according to the present invention.

By way of example, the collar member 40 and luer wall 34 may be configured to provide a tactile feel when the male luer 30 has been fully engaged to the LAD 10. As shown in shadow in FIG. 3 the luer wall may include some detents 13 which are placed so as to register with one of cavities or openings 11 formed in the collar member 40. To allow the LAD to connect with standard male luers, the detents 13 may be placed lower on the luer wall 34 and the collar member 40 extended to provide the registration.

The inlet 18 fixedly receives a fluid flow controller 44 having a resealable slit or aperture 46 therethrough. The flow controller 44 acts as a microbial barrier between the internal passageway 22 of the LAD 10 and the atmosphere. The flow controller 44 may include a substantially concave upper surface 48 (FIG. 1), which provides a relatively tight seal of the aperture 46. Alternatively, the upper surface 48a may be substantially flat (FIG. 7), such that it can be easily wiped with antiseptic, which aids in preventing contamination during use.

Figure 2:
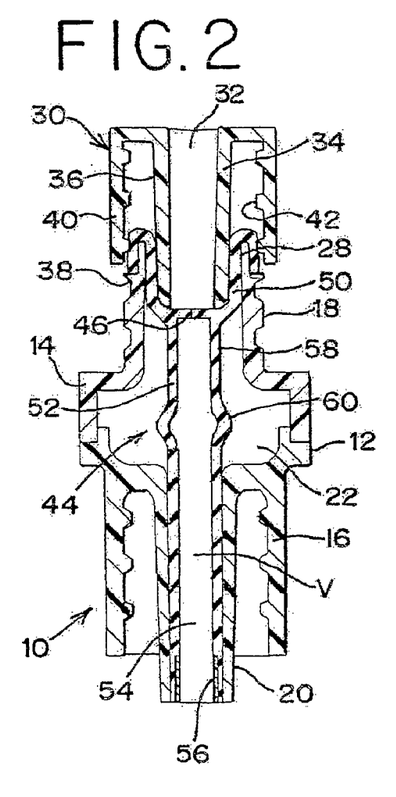
FIG. 2 is a cross-sectional view of the LAD of FIG. 1, with a male luer partially inserted therein.
Figure 3:
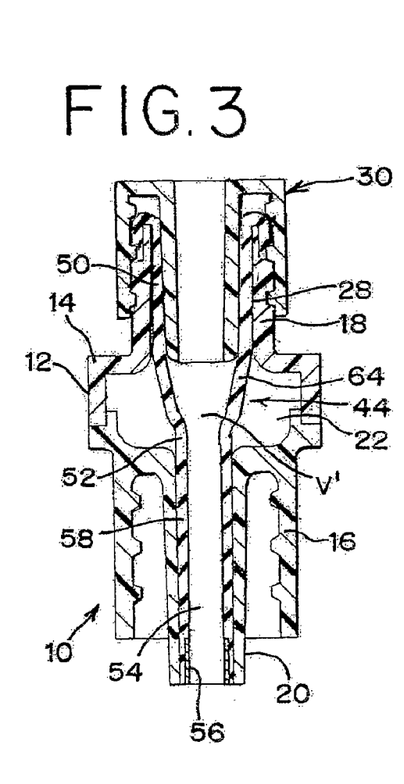
FIG. 3 is a cross-sectional view of the LAD of FIG. 1, with a male luer fully inserted therein.

The flow controller 44 is comprised of a first portion or valve element 50, which includes the upper surface 48 and the aperture 46, and a second portion or extending portion 52 (FIG. 1) that extends away from the valve element 50. The extending portion 52 is generally tubular and defines a fluid flow path 54 in communication with the aperture 46 of the valve element 50. The valve element 50 is fixedly attached to the LAD inlet 18, while the extending portion 52 is fixedly attached to the LAD outlet 20, preferably by mechanical means, such as a bushing member 56. The operation of the flow controller 44 is illustrated in FIGS. 2 and 3, and will be described in greater detail herein.

Figure 4:
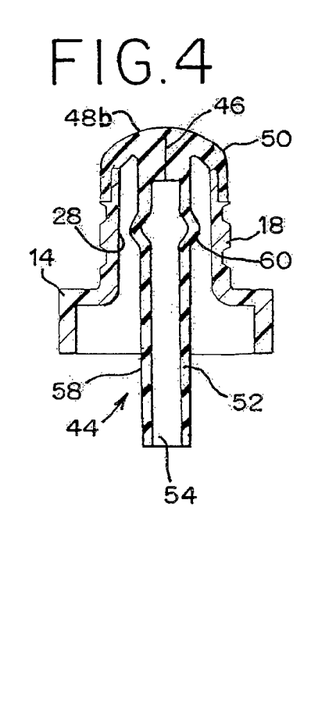
FIGS. 4-7 show a method of manufacturing the LAD of FIG. 1.

Preferably, the flow controller 44 is molded as a unitary piece, typically from a deformable elastomeric material, such as silicone or rubber or santoprene. The "as-molded" configuration of the flow controller 44 is shown in FIG. 4, with a substantially convex upper surface 48b and an extending portion 52 comprised of a wall 58 having a bulb or bulge 60. The illustrated wall 58 has a generally uniform outer radius, except for the bulge 60, which has an increased outer radius. The bulge 60 affects the flow dynamics of the LAD 10, as will be described in greater detail herein.

It will be seen that the flow controller 44 is significantly shorter in the "as-molded" configuration of FIG. 4, as compared to the condition illustrated in FIG. 1. According to a preferred method of manufacturing the flow controller 44, the flow controller 44 is initially provided in the relatively short "as-molded" condition of FIG. 4, along with a separate upper valve housing portion 14. The valve element 50 is fixedly attached to the LAD inlet 18 to close the opening 28 thereof. This may be done by any of a number of means, which vary according to the materials selected for the flow controller 44 and the upper housing portion 14. These means include, but are not limited to, adhesion or mechanical attachment (e.g., crimping), although the flow controller 44 is preferably over-molded onto the upper housing portion 14. The aperture 46 may be formed in the valve element 50 prior to or after the valve element 50 is secured to the LAD inlet 18. Referring briefly to FIG. 2, the overmolded section attaching the controller 44 and the upper housing portion 14, may be dimensioned to engage the threads of the male luer to provide the desired torque resistance to disengagement per ISO standards.

Figure 5:
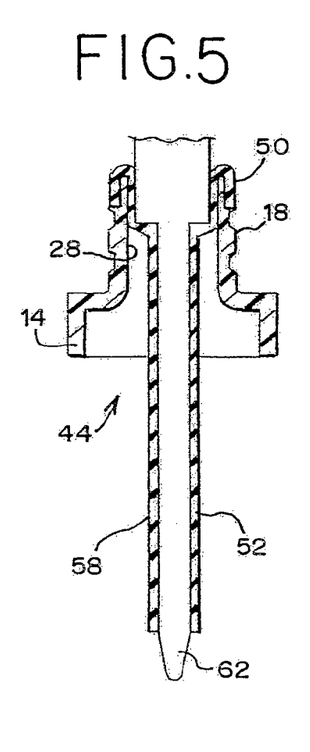

When the valve element 50 has been secured to the inlet 18, an elongated mandrel or vacuum member 62 is inserted through the aperture 46 and the fluid flow path 54 (FIG. 5). A suction source (not illustrated) is associated with the mandrel 62 and creates a vacuum force that pulls the extending portion 52 inwardly against the mandrel 62. The mandrel 62 is then moved downwardly (in the orientation of FIG. 5) to push the convex upper surface 48b into the LAD inlet 18 and stretch the extending portion 52. In the "fully stretched" condition of FIG. 5, the bulge 60 substantially flattens out against the mandrel 62 and the wall 58 of the extending portion 52 has a generally uniform outer radius. It will be appreciated that the flow controller 44, and in particular the extending portion 52 is in a state of tension in the "fully stretched" condition of FIG. 5.

Figure 6:
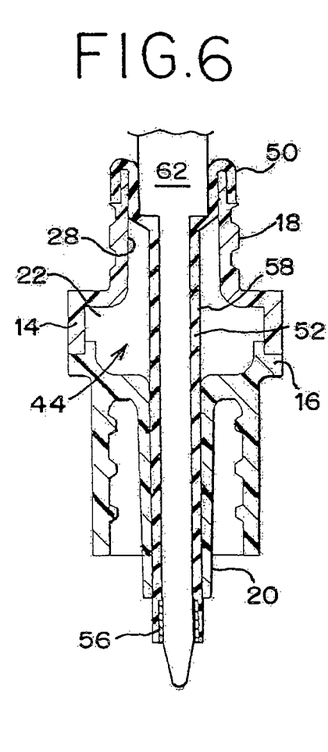
Figure 7:
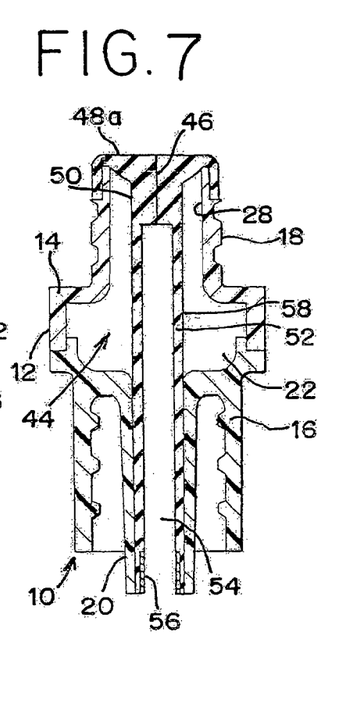

With the mandrel 62 still in place and providing a suction force, the lower valve housing portion 16 is slid over the extending portion 52 and affixed to the upper housing portion 14 (FIG. 6). A portion of the mandrel 62 and the extending portion 52 remains outside of the lower housing portion 16. A bushing member 56 is affixed to this portion of the extending portion 52, and the mandrel 62 is removed (FIG. 7). When the mandrel 62 has been removed, the flow controller 44 is free to move into an "assembled" condition (FIGS. 1 and 7). The flow controller 44 as a whole shifts upwardly and the upper surface 48 assumes either a concave condition (FIG. 1) or a flat condition (FIG. 7) depending on the magnitude of the original convex curvature (FIG. 4) and the degree of stretching. Forcing the upper surface 48 to fit within the inlet opening 28 forces the valve element into a state of radial compression, which promotes an improved seal of the resealable aperture 46, thereby preventing fluid leakage through the inlet 18. The bushing member 56 constrains the extending portion 52, thereby maintaining it in a state of tension, and preventing it from returning to the "as-molded" condition of FIG. 4. From FIG. 7, it will be seen that the fluid flow path 54 is isolated from the surrounding LAD passageway 22 to define the sole path for fluid moving through the LAD 10.

In an alternate embodiment, the extending portion 52 may be directly attached to the lower valve housing portion 52 by over-molding.

Turning now to the operation of the LAD 10, a male luer 30 is inserted into the inlet 18 and through the aperture 46 (FIG. 2). If desired, the aperture 46 or the male luer 30 may be lubricated for ease of insertion and removal. The male luer 30 deforms the flow controller 44 and relieves some of the tension in the extending portion 52. On account of the shape memory of the elastomeric material, this reduction in tension allows the bulge 60 to reemerge and expand outwardly into the surrounding passageway 22, thereby defining a first volume V of the fluid flow path 54.

The male luer 30 is further inserted into the aperture 46 until the aperture 46 completely opens and allows a portion of the male luer 30 to move into the extending portion 52. The outer radius of the male luer 30 is larger than the inner radius of the fluid flow path 54, which causes the portion of the wall 58 between the bulge 60 and the male luer 30 to bend outward into a generally frusto-conical shape defining a fluid reservoir 64 (FIG. 3). When the fluid reservoir 64 has been established and the male luer 30 is fully inserted, a second volume V' is defined.

The difference between the first volume V (FIGS. 1 and 2) and the second volume V' (FIG. 3) determines the magnitude of the fluid displacement when the male luer 30 is inserted and removed, and that difference is determined by the configuration of the bulge 60. Reflux of fluid into the male luer 30 can lead to a number of problems, such as contamination, so it may be preferred for the bulge 60 to be adapted such that the difference between the first volume V and the second volume V' is minimized. In one embodiment, the bulge 60 is adapted such that the first volume V is substantially equal to the second volume V', which ideally creates a neutral fluid displacement, thereby substantially eliminating fluid reflux when the male luer 30 is inserted or removed. If the volumes V and V' cannot be practicably equated, then preferably the bulge 60 is adapted such that the second volume V' is only slightly smaller than the first volume V, which results in a minor positive fluid displacement as the male luer 30 is inserted into the LAD 10 and a minor negative fluid displacement as the male luer 30 is removed from the LAD 10.

Figure 8:
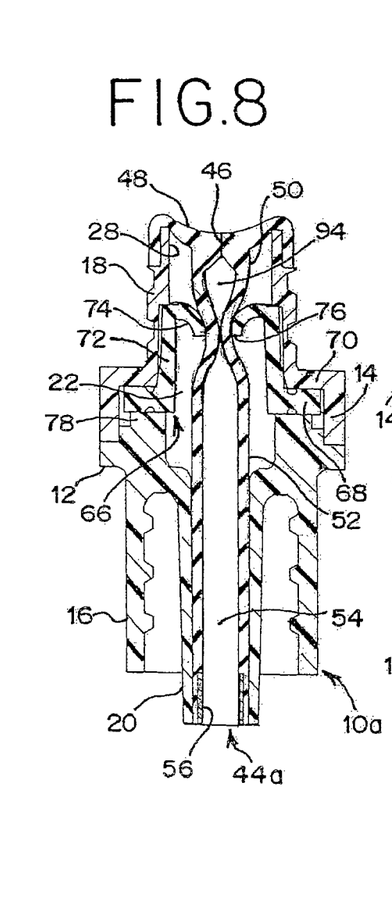
FIG. 8 is a cross-sectional view of another embodiment of an LAD according to the present invention.

FIG. 8 illustrates another LAD 10a according to the present invention. The LAD 10a of FIG. 8 generally conforms to the foregoing description of the embodiment of FIG. 1, except it includes a restrictor member 66 mounted within the valve housing 12. The restrictor member 66 acts as a second or auxiliary resealable aperture, as will be described in greater detail herein.

Figure 10:
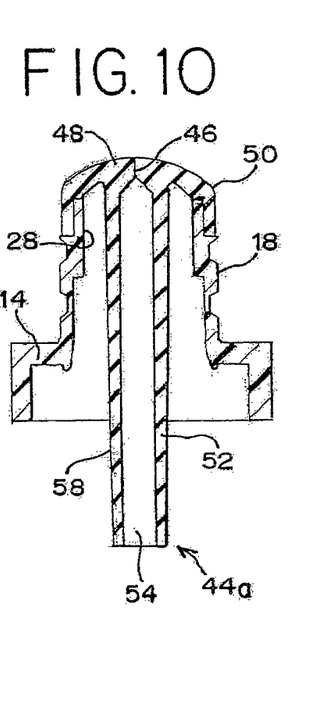
FIGS. 10-13 show a method of manufacturing the LAD of FIG. 8.

As with the embodiment of FIG. 1, the flow controller 44a is preferably molded as a unitary piece, typically from a deformable elastomeric material, such as silicone or rubber or santoprene. With the flow controller 44a in an "as-molded" configuration, the valve element 50 is secured to the LAD inlet 18 (FIG. 10) to close the opening 28 thereof. This may be done by any of a number of means, which vary according to the materials selected for the flow controller 44a and the upper housing portion 14. These means include, but are not limited to, adhesion or mechanical attachment (e.g., crimping), although the flow controller 44a is preferably over-molded onto the upper housing portion 14. In FIG. 10, the extending portion 52 of the flow controller 44a is illustrated without a bulge, but a bulge may also be provided without departing from the scope of the present invention.

Figure 11:
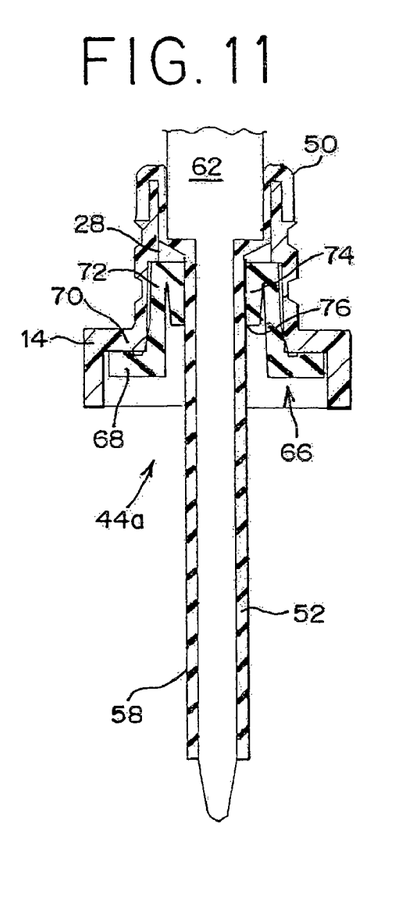

When the valve element 50 has been secured to the inlet 18, an elongated mandrel or vacuum member 62 is inserted through the aperture 46 and the fluid flow path 54 (FIG. 11).

A suction source (not illustrated) is associated with the mandrel 62 and creates a vacuum force that pulls the extending portion 52 inwardly against the mandrel 62. The mandrel 62 is then moved downwardly (in the orientation of FIG. 11) to push the convex upper surface 48b into the LAD inlet 18, stretch the extending portion 52, and maintain the flow controller 44a in a state of tension.

With the mandrel 62 still in place and providing a suction force, the restrictor member 66 is slid over the extending portion 52 and into the position of FIG. 11. In the illustrated embodiment, the restrictor member 66 has an annular rim 68 adapted to abut a shoulder 70 of the upper housing portion 14. A generally tubular portion 72 extends upwardly from the rim 68 and terminates in an inwardly extending upper flange 74. In a relaxed condition (FIG. 8), the flange 74 defines an opening 76 smaller than the diameter of the extending portion 52 to compress and close the fluid flow path 54, but the presence of the mandrel 62 widens the opening 76 into an open condition (FIG. 11). The profile of the opening 76 may vary, provided that it is adapted to close the fluid flow path 54 in the relaxed condition of FIG. 8 and to allow passage of the fluid flow path 54 in the open condition of FIG. 11.

As described in greater detail herein, the flange 74 has the tendency to resiliently return to the relaxed condition when the mandrel 62 is removed from the LAD 10a. Accordingly, the flange 74 is preferably comprised of a material more rigid than the elastomeric material of the flow controller 44a (to pinch the fluid flow path 54 closed), but sufficiently pliable to move between the relaxed condition of FIG. 8 and the open condition of FIGS. 9B and 11. Suitable materials for the flange 74, and preferably the entire restrictor member 66, include rubber, silicone, polyisoprene, HDPE and polyurethane It will be seen from the following description that the restrictor member 66 may be provided in virtually any configuration, provided that it includes means for holding it in place within the LAD 10a and means for resiliently compressing a section of the fluid flow path 54 into a closed position (FIGS. 8 and 9A).

Figure 12:
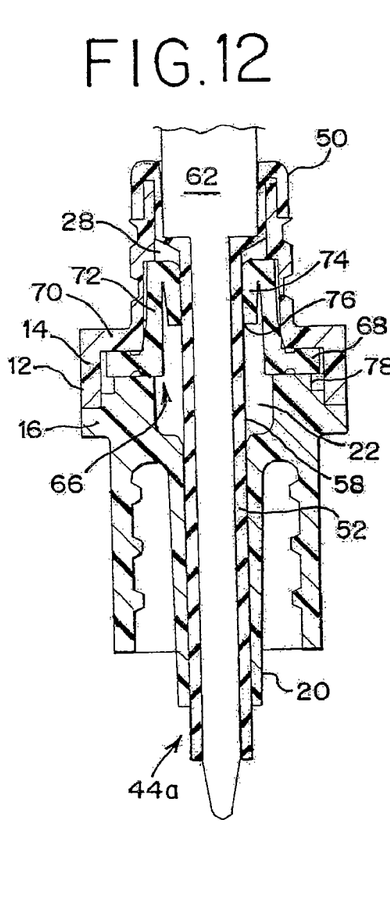

When the restrictor member 66 has been properly positioned within the upper housing portion 14, the lower valve housing portion 16 is slid over the extending portion 52 and affixed to the upper housing portion 52 (FIG. 12). Preferably, the lower housing portion 16 includes an element, illustrated in FIG. 12 as an upwardly extending annular lip 78, which abuts the restrictor member rim 68 and maintains the restrictor member 66 in place. However, other means for maintaining the restrictor member 66 in place within the housing 12 may be used without departing from the scope of the present invention.

Figure 13:
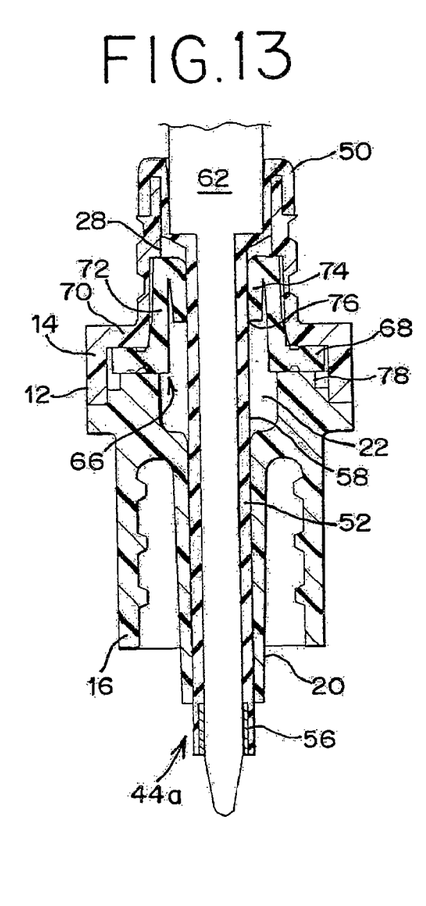

A portion of the mandrel 62 and the extending portion 52 remains outside of the lower housing portion 16. A bushing member 56 is affixed to this portion of the extending portion 52 (FIG. 13), and the mandrel 62 is removed (FIG. 8). When the mandrel 62 has been removed, the flow controller 44a is free to move into an "assembled" condition (FIG. 8), according to the foregoing description of the embodiment of FIG. 1. Additionally, the flange 74 of the restrictor member 66 resiliently returns to its relaxed condition, thereby decreasing the size of the opening 76 and pinching closed a section of the fluid flow path 54.

Figure 9A:
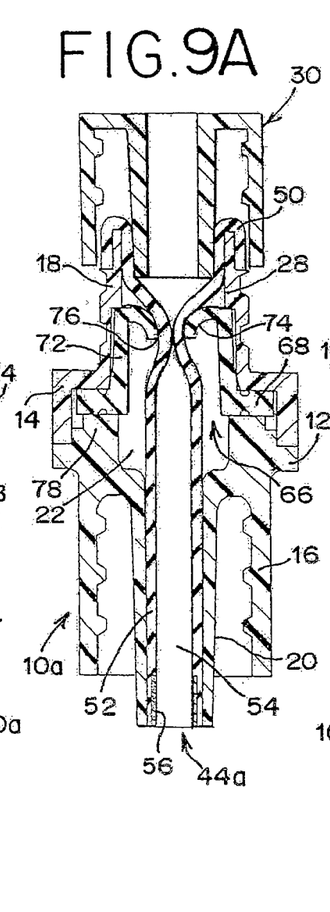
FIG. 9A is a cross-sectional view of the LAD of FIG. 8, with a male luer partially inserted therein.
Figure 9B:
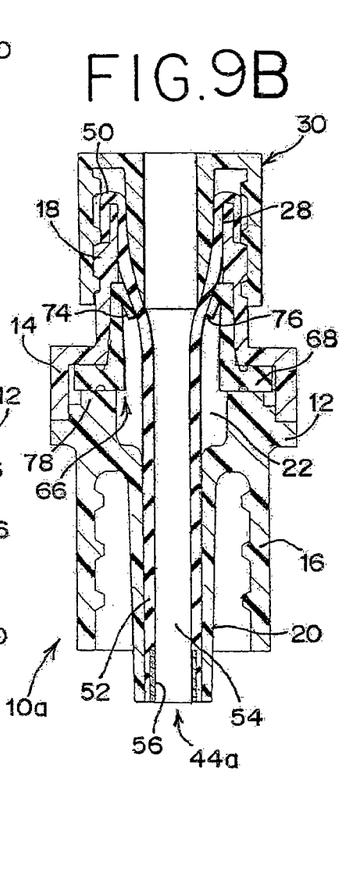
FIG. 9B is a cross-sectional view of the LAD of FIG. 8, with a male luer fully inserted therein.

Turning now to the operation of the LAD 10a, a male luer 30 is partially inserted into the inlet 18 and through the aperture 46 (FIG. 9A). The male luer 30 opens the aperture 46, but not the opening 76 of the restrictor member 66, so flow through the LAD inlet 18 remains closed (FIG. 9A). Hence, it will be seen that the restrictor member 66 acts as a secondary or auxiliary sealing element that prevents fluid flow through the inlet 18 when the male luer 30 is only partially inserted. As the male luer 30 is further inserted into the inlet 18, it engages the section of the fluid flow path 54 closed by the restrictor member 66 and forces the restrictor member 66 into the open condition of FIG. 9B. In the condition of FIG. 9B, fluid flow through the LAD 10a may begin. If the extending portion 52 includes a bulge (not illustrated), the fluid displacement upon inserting and removing the male luer 30 will be governed according to the foregoing description of the embodiment of FIG. 1.

Similarly upon withdrawal of the male luer 30, as the male luer is withdrawn the male luer no longer engages the section of the fluid flow path 54 adjacent the restrictor member 66 and the restrictor member then closes the flow path. Further withdrawal of the male luer will create a vacuum condition in the flow path 54 which pulls fluid from within the male luer. This reduces aersolization of fluid from the male luer tip.

Figures 14, 15:
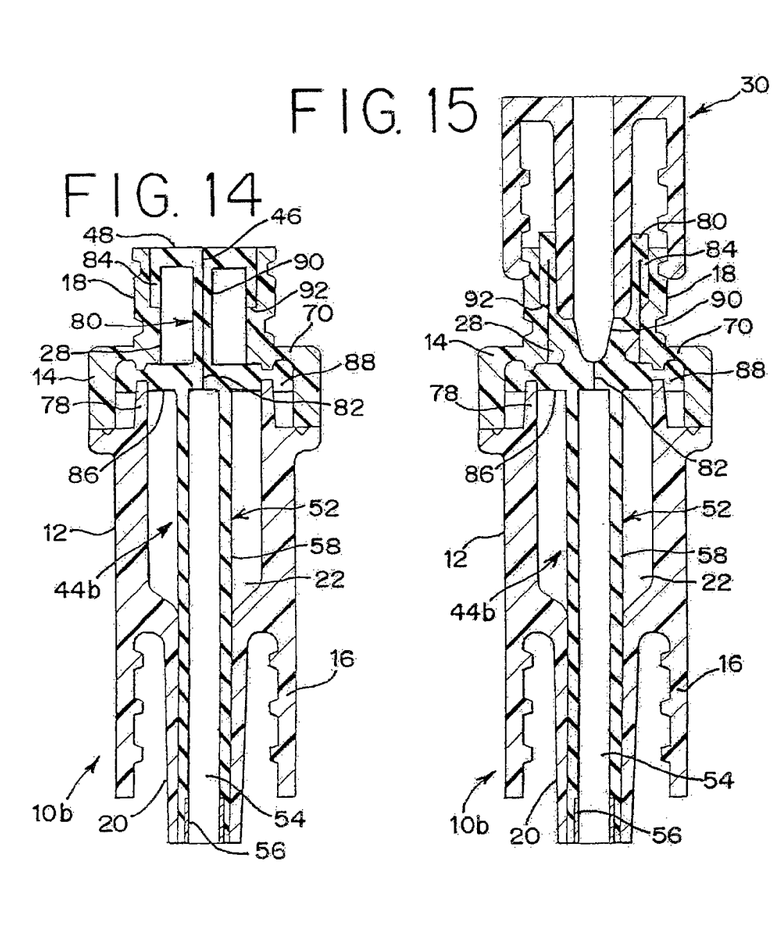
FIG. 14 is a cross-sectional view of another embodiment of an LAD according to the present invention.
FIG. 15 is a cross-sectional view of the LAD of FIG. 14, with a male luer partially inserted therein.

FIG. 14 illustrates yet another LAD 10b according to the present invention. The LAD 10b of FIG. 14 generally conforms to the foregoing description of the embodiment of FIG. 1, except it includes a modified valve element 80. The modified valve element 80 provides a second or auxiliary resealable aperture 82, similar to the embodiment of FIG. 8, but it may be preferred for some applications because it eliminates the potential non-flushable "dead space" between the upper and lower sealing elements, as described in greater detail herein.

As with the embodiment of FIG. 1, the flow controller 44b is preferably molded as a unitary piece (FIG. 17), typically from a deformable elastomeric material, such as silicone or rubber or santoprene. The modified valve element 80 includes an upper surface or first sealing layer 48 defining a first resealable aperture 46 adapted to receive a male luer 30 (FIG. 15). In the illustrated embodiment, a skirt 84 extends downwardly from the outer perimeter of the first sealing layer 48. A second sealing layer 86 is spaced from the first sealing layer 48 and includes a rim 88 comparable in structure and operation to the restrictor member rim 68 of the embodiment of FIG. 8. The rim 88 defines a second resealable aperture 82 adapted to receive a male luer 30 (FIG. 16) and preferably coaxial with the first aperture 46. The first and second apertures 46 and 82 are joined by a channel 90. As shown in FIG. 17, the channel 90 is preferably at least partially open in the "as-molded" configuration. The flow controller 44b is illustrated in FIG. 17 with a flat upper surface 48 and a bulge 60, but it will be appreciated from the following description that the upper surface 48 may be substantially convex in the "as-molded" configuration and/or the extending portion 52 may be provided without the bulge 60.

With the flow controller 44b in an "as-molded" configuration, the modified valve element 80 is secured to the LAD inlet 18 (FIG. 18) to close the opening 28 thereof. This may be done by any of a number of means, but is preferably achieved by pushing the upper surface 48 upward through the inlet 18 until the skirt 84 seats within a ledge or shelf 92 of the inlet 18 by a friction fit. Preferably, the upper surface 48 is slightly larger than the inlet 18, such that the upper surface 48 is seated with an interference fit that results in a radial compression that aids in more tightly sealing the first aperture 46.

Figures 18, 19:
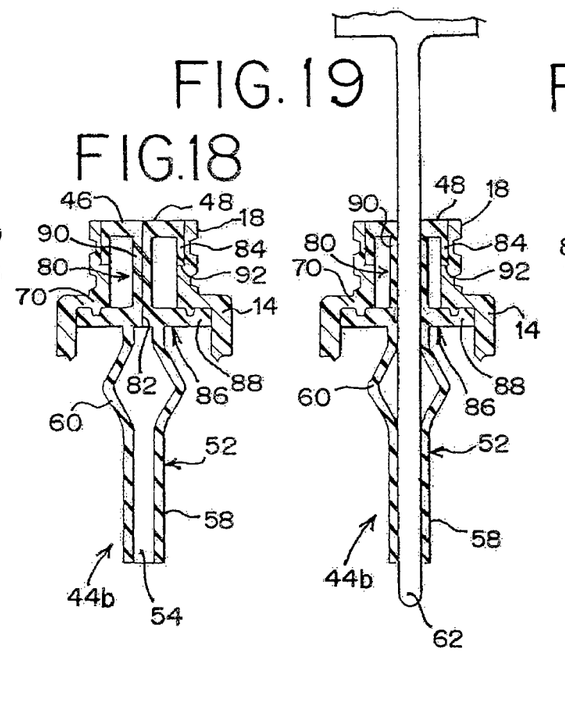

When the first sealing layer 48 is securely seated, the rim 88 is positioned to abut a shoulder 70 of the upper housing portion 14. The rim 88 may be affixed to the shoulder 70 by a variety of means, depending on the material selected for the housing upper portion 14 and the flow controller 44b. Suitable means may include welding, adhesion, and a press fit with the lower housing portion 16, as described in greater detail herein.

Preferably, the distance between the top of the upper surface 48 and the rim 88 is less than the height of the inlet 18, such that the channel 90 must be stretched to properly position the first and second sealing layers 48 and 86. FIG. 18 shows that a channel 90 in such a state of tension will deform to be substantially closed, along with the first aperture 46 and the second aperture 82. Stretching the channel 90 may cause the first and/or second sealing layers to assume a generally concave configuration (not illustrated) that imparts a radial compression on the associated apertures and aids in maintaining the inlet 18 in a sealed condition.

Figure 20:
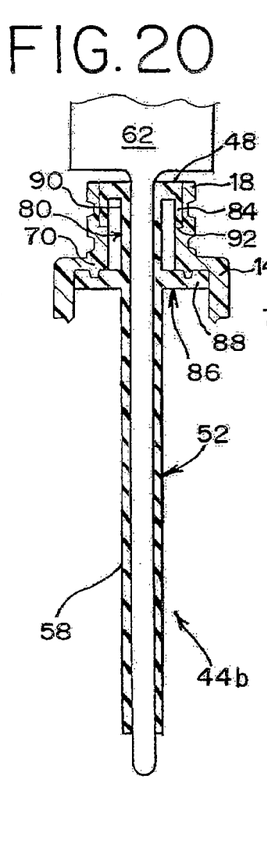

When the modified valve element 80 has been secured to the inlet 18, an elongated mandrel or vacuum member 62 is inserted through the apertures 46 and 82, the channel 90, and the fluid flow path 54 (FIG. 19). A suction source (not illustrated) is associated with the mandrel 62 and creates a vacuum force that pulls the extending portion 52 and bulge 60 inwardly against the mandrel 62. The mandrel 62 is then moved downwardly (in the orientation of FIG. 20) to stretch the extending portion 52 and maintain the flow controller 44b in a state of tension.

Figure 21:
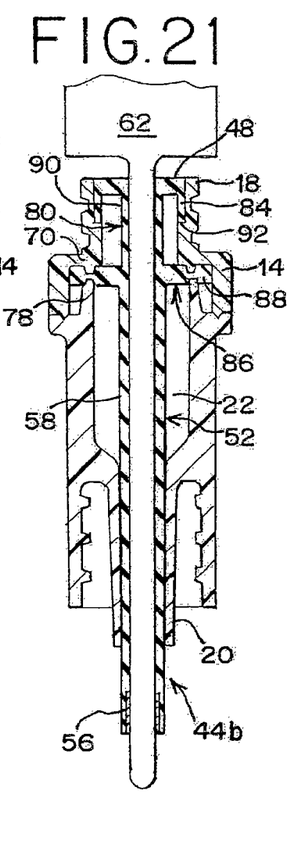
Figure 22:
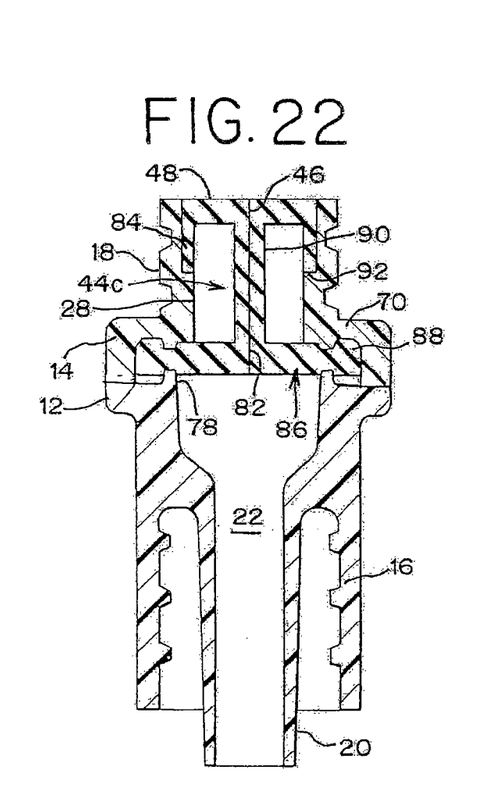
FIG. 22 is a cross-sectional view of a variation of the LAD of FIG. 14.
Figure 23:
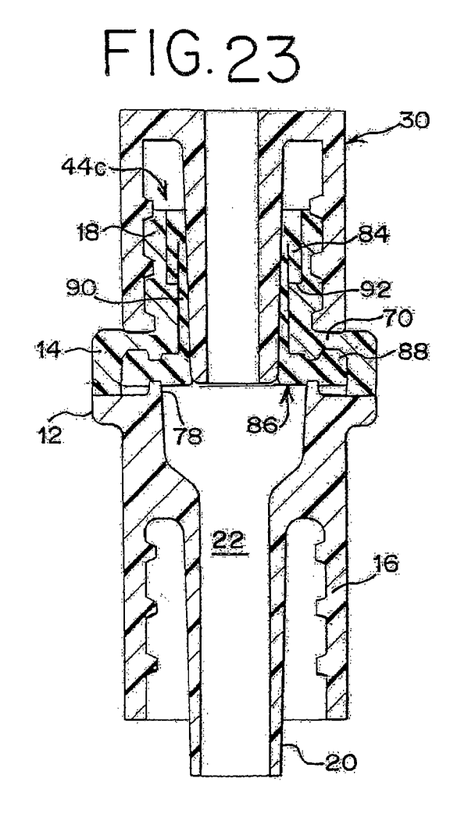
FIG. 23 is a cross-sectional view of the LAD of FIG. 22, with a male luer fully inserted therein.

With the mandrel 62 still in place and providing a suction force, the lower housing portion 16 is slid over the extending portion 52 and affixed to the upper housing portion 14 (FIG. 21). Preferably, the lower housing portion 16 includes an element, illustrated in FIG. 21 as an upwardly extending annular lip 78, which compresses the second sealing layer rim 88 and maintains the second sealing layer 86 in place. This may be done instead of or in addition to welding or otherwise securing the rim 88 to the shoulder 70 in the condition of FIG. 18. However, in comparison to the restrictor member rim 68 of FIG. 8, the second sealing layer 86 is relatively flexible, so it may be preferred to use two joinder means (e.g., welding and a compression relationship) to ensure that the second sealing layer 86 is securely maintained within the LAD housing 12.

A portion of the mandrel 62 and the extending portion 52 remains outside of the lower housing portion 16. A bushing member 56 is affixed to this portion of the extending portion 52 (FIG. 21), and the mandrel 62 is removed (FIG. 14). When the mandrel 62 has been removed, the flow controller 44b is free to move into an "assembled" condition (FIG. 14), according to the foregoing description of the embodiment of FIG. 1. Additionally, the channel 90 and the second aperture 82 will resiliently close to seal the inlet 18, along with the first aperture 46.

Turning now to the operation of the LAD 44b, a male luer 30 is partially inserted into the inlet 18 and through the first aperture 46 (FIG. 15). The male luer 30 opens the aperture 46 and at least a portion of the channel 90, but not the second aperture 82, so flow through the LAD inlet 18 remains closed. Hence, it will be seen that the second sealing layer 86 acts as a secondary or auxiliary sealing element that prevents fluid flow through the inlet 18 when the male luer 30 is only partially inserted.

Figure 16:
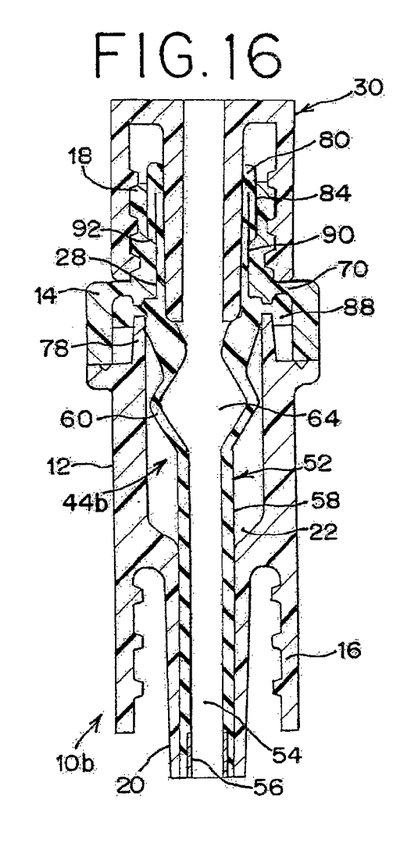
FIG. 16 is a cross-sectional view of the LAD of FIG. 14, with a male luer fully inserted therein.
Figure 17:
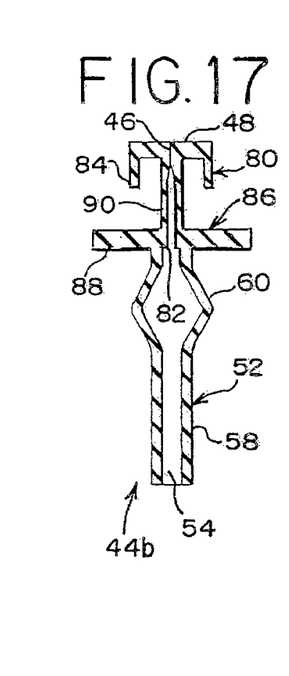
FIGS. 17-21 show a method of manufacturing the LAD of FIG. 14.

As the male luer 30 is further inserted into the inlet 18, it continues to deform the flow controller 44b, which causes the bulge 60 to reemerge, and opens the second aperture 82 (FIG. 16). In the condition of FIG. 16, fluid flow through the LAD 10b may begin. Depending on the nature of the bulge 60 and the resulting fluid reservoir 64, insertion or removal of the male luer 30 will result in a positive, negative, or neutral fluid displacement, according to the foregoing description of the embodiment of FIG. 1.

It will be appreciated that the embodiment of FIG. 8 similarly provides a second sealing element (the restrictor member opening 76). However, the embodiment of FIG. 14, which provides a substantially closed channel 90 between the upper and lower sealing layers 48 and 86, may be preferred for certain applications.

Figure 24:
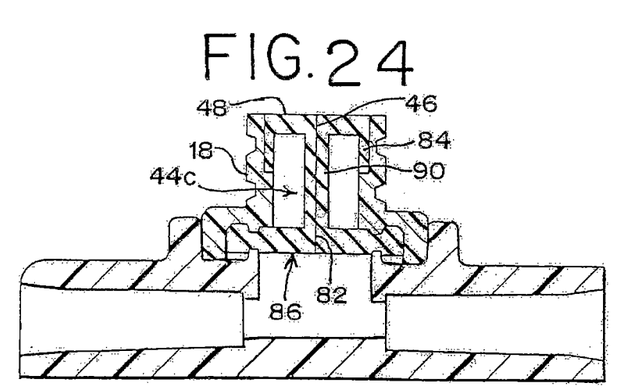
FIG. 24 is a cross-sectional view of a portion of the LAD of FIG. 22 incorporated into a T-site.
Figure 25:
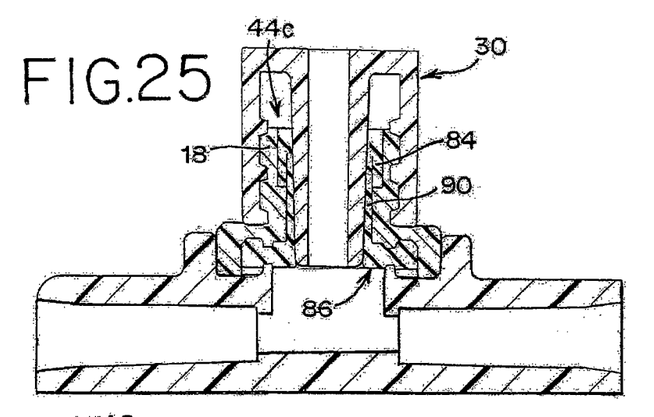
FIG. 25 is a cross-sectional view of the device of FIG. 24, with a male luer fully inserted into the T-site.
Figure 26:
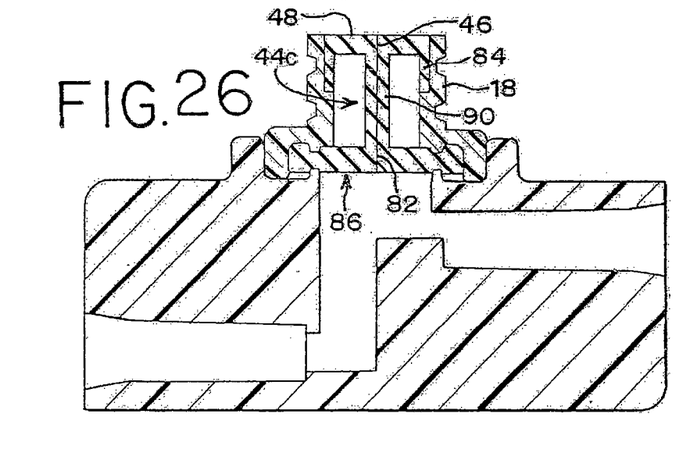
FIG. 26 is a cross-sectional view of a portion of the LAD of FIG. 22 incorporated into another T-site.

The flow controller 44b of FIG. 14 may be modified by removing the extending portion 52 and leaving only the valve element 80, as shown in FIGS. 22-26. The resulting flow controller 44c may be incorporated as a valve of any of a number of devices, including LAD's as described herein (FIGS. 22 and 23) and T-sites (FIGS. 24-26). Such a flow controller 44c may be preferred to known single or double slit septum-type valves, because there are two separate sealing layers 48 and 86, along with a channel 90 therebetween that is substantially closed in a relaxed condition (FIGS. 22, 24, and 26) to prevent the creation of a "dead space."

Referring in particular to FIG. 26, flow flows through the channel formed by the housing in a path which causes any air present in the injection site to be displaced out of the housing. This provides a self flushing feature to the valve.

While the present invention has been described in terms of certain preferred and alternative embodiments for purposes of illustration, it is not limited to the precise embodiments shown or to the particular features, shapes or sizes illustrated. A variety of changes may be made without departing from the present invention as defined by the appended claims.

The invention claimed is:

1. A medical valve for the bi-directional transfer of fluid comprising:
    a valve housing having an inlet adapted for receiving a male luer, an outlet and a passageway therethrough; and
    a fluid flow controller received within the valve housing, said fluid flow controller having
        a valve element fixedly attached to said inlet, said valve element having a resealable aperture for receiving the male luer and sealing the inlet, and
        an extending portion extending away from the valve element and fixedly attached to said outlet, said extending portion defining (i) a fluid flow path in communication with said aperture and said outlet (ii) a generally tubular wall, and (iii) a bulge,
    wherein (a) said fluid flow controller is maintained in a tensioned state within the valve housing, (b) the bulge has a radius larger than a radius of the tubular wall in an untensioned state, and substantially the same radius as the radius of the tubular wall in the tensioned state, and (c) insertion of the male luer into the inlet (1) decreases the tension in at least a portion of the fluid flow controller, (2) changes a volume of said fluid flow controller, and (3) causes the bulge to radially expand to define a fluid reservoir.

2. The medical valve of claim 1, wherein said change in volume results in substantially no fluid displacement when the male luer is inserted or removed from the inlet.

3. The medical valve of claim 1, wherein said change in volume results in a positive displacement of fluid as the male luer is inserted into the inlet.

4. The medical valve of claim 1, wherein the valve element of the fluid flow controller includes a first seating layer defining a first aperture, a second sealing layer defining a second aperture, and a channel therebetween and in communication with said apertures, wherein said channel is substantially closed in a tensioned state and open in an untensioned state.

5. The medical valve of claim 1 in which at least a portion of the fluid flow controller is overmolded onto the valve housing.

6. The medical valve of claim 1 in which at least a portion of the fluid flow controller is mechanically attached to the valve housing.

7. The medical valve of claim 1, further including a restrictor member that resiliently closes a section of the fluid flow path, said restrictor member adapted to open said section of the fluid flow path to open when the male luer is inserted into the fluid flow controller.

8. The medical valve of claim 7 in which the restrictor member compresses the extending portion to close the section of the fluid flow path.

9. The medical valve of claim 8 in which the restrictor member includes an opening and said extending portion of the fluid controller extends through said opening.

10. A medical valve comprising:
   a valve housing having
      (i) an inlet adapted for receiving a male luer,
      (ii) an upper housing portion, and
      (iii) a lower housing portion, the lower housing portion defining an outlet; and
   a fluid flow controller associated with the valve housing, the fluid flow controller having
      (i) an extending portion defined by a generally tubular wall and a bulge, the extending portion fixedly attached to the outlet in a tensioned state, and
      (ii) a valve element fixedly attached to said inlet in the tensioned state,
      wherein (a) the extending portion defines a fluid flow path, and (b) the bulge has a larger radius than a radius of the tubular wall in an untensioned state and substantially the same radius as the radius of the tubular wall in the tensioned state,
   said valve element having
      (i) a first sealing layer defining a first resealable aperture,
      (ii) a second sealing layer defining a second resealable aperture,
         wherein (a) a portion of the second sealing layer is compressed between the upper housing portion and the lower housing portion to attach the second sealing layer to the housing, (b) the extending portion extends away from the second sealing layer, and (c) the fluid flow path is in communication with the second aperture and the outlet, and
      (iii) a channel therebetween and in communication with said apertures, wherein said channel is substantially closed in the tensioned state and open in the untensioned state,
   wherein insertion of the male luer into the inlet (a) changes a volume of the fluid flow path, and (b) causes the bulge to radially expand to define a fluid reservoir.

11. The medical valve of claim 10 in which the tension in the channel causes at least one of the first and second sealing layers to have a concave configuration.

12. The medical valve of claim 10 in which the first sealing layer is attached to the valve housing by an interference fit.

13. The medical valve of claim 10 in which the first sealing layer includes a downwardly extending skirt adapted to form a friction fit with the valve housing to attach the first sealing layer to the housing.

14. The medical valve of claim 10, wherein said change in volume results in substantially no fluid displacement when the male luer is inserted or removed from the inlet.

15. The medical valve of claim 10, wherein said change in volume results in a positive displacement of fluid as the male luer is inserted into the inlet.

* * * * *